US008764833B2

(12) United States Patent
de Villiers et al.

(10) Patent No.: US 8,764,833 B2
(45) Date of Patent: Jul. 1, 2014

(54) ARTIFICIAL INTERVERTEBRAL DISC WITH LOWER HEIGHT

(75) Inventors: Malan de Villiers, Wapadrand (ZA); Neville Jansen, Waterkloof (ZA); Yves Arramon, Sunnyvale, CA (US)

(73) Assignee: SpinalMotion, Inc., Mountain View, CA (US)

(*) Notice: Subject to any disclaimer, the term of this patent is extended or adjusted under 35 U.S.C. 154(b) by 415 days.

(21) Appl. No.: 12/400,221

(22) Filed: Mar. 9, 2009

(65) Prior Publication Data
US 2009/0234458 A1 Sep. 17, 2009

Related U.S. Application Data

(60) Provisional application No. 61/069,048, filed on Mar. 11, 2008.

(51) Int. Cl.
*A61F 2/44* (2006.01)
(52) U.S. Cl.
USPC .................. 623/17.16; 623/17.15; 623/17.11
(58) Field of Classification Search
USPC ..................... 623/17.11–17.16; 606/246–249
See application file for complete search history.

(56) References Cited

U.S. PATENT DOCUMENTS

| | | |
|---|---|---|
| 3,486,505 A | 12/1969 | Morrison |
| 3,867,728 A | 2/1975 | Stubstad et al. |
| 4,309,777 A | 1/1982 | Patil |
| 4,531,917 A | 7/1985 | Linkow et al. |
| 4,566,466 A | 1/1986 | Ripple et al. |
| 4,619,660 A | 10/1986 | Christiansen et al. |
| 4,673,407 A | 6/1987 | Martin |
| 4,759,766 A | 7/1988 | Buettner-Janz et al. |

(Continued)

FOREIGN PATENT DOCUMENTS

| | | |
|---|---|---|
| DE | 3023353 | 4/1981 |
| EP | 0 333 990 | 9/1989 |

(Continued)

OTHER PUBLICATIONS

International Search Report and Written Opinion of PCT Application No. PCT/US2009/036687, dated May 5, 2009, 8 pages total.

(Continued)

*Primary Examiner* — Mary Hoffman
*Assistant Examiner* — Christina Negrellirodrigue
(74) *Attorney, Agent, or Firm* — Wilson Sonsini Goodrich & Rosati

(57) ABSTRACT

An intervertebral disc is provided having an upper plate, a lower plate, and a core. The upper and lower plates include outer vertebral body contacting surfaces which are provided with attachment enhancing features to ensure bone integration. The attachment enhancing features shown include one or more fins, serrations and teeth. An opposite surface of the plates from the vertebral body contacting surfaces is formed with a recess which serves as a bearing surface for the core. In order to form an intervertebral disc with a lower disc height, at least one of the recesses is provided opposite a corresponding dome shaped portion on the vertebral body contacting surfaces. This allows the plates to be formed with a thinner profile for a smaller overall disc height. In addition to providing a lower overall height to the artificial disc, the dome shaped portion of the plates also provides a more anatomically shaped outer vertebral body contacting surface.

14 Claims, 3 Drawing Sheets

(56) References Cited

U.S. PATENT DOCUMENTS

| | | |
|---|---|---|
| 4,759,769 A | 7/1988 | Hedman et al. |
| 4,834,757 A | 5/1989 | Brantigan |
| 4,863,477 A | 9/1989 | Monson |
| 4,904,261 A | 2/1990 | Dove et al. |
| 4,917,704 A | 4/1990 | Frey et al. |
| 4,932,969 A | 6/1990 | Frey et al. |
| 4,997,432 A | 3/1991 | Keller |
| 5,035,716 A | 7/1991 | Downey |
| 5,057,108 A | 10/1991 | Shetty et al. |
| 5,071,437 A | 12/1991 | Steffee |
| 5,122,130 A | 6/1992 | Keller |
| 5,195,526 A | 3/1993 | Michelson |
| 5,258,031 A | 11/1993 | Salib et al. |
| 5,282,861 A | 2/1994 | Kaplan |
| 5,314,477 A | 5/1994 | Marnay |
| 5,320,644 A | 6/1994 | Baumgartner |
| 5,370,697 A | 12/1994 | Baumgartner |
| 5,401,269 A | 3/1995 | Buttner-Janz et al. |
| 5,415,704 A | 5/1995 | Davidson |
| 5,458,642 A | 10/1995 | Beer et al. |
| 5,462,575 A | 10/1995 | Del Corso |
| 5,484,437 A | 1/1996 | Michelson |
| 5,489,307 A | 2/1996 | Kuslich et al. |
| 5,505,732 A | 4/1996 | Michelson |
| 5,507,816 A | 4/1996 | Bullivant |
| 5,534,030 A | 7/1996 | Navarro et al. |
| 5,556,431 A | 9/1996 | Buttner-Janz |
| 5,674,296 A | 10/1997 | Bryan et al. |
| 5,676,701 A | 10/1997 | Yuan et al. |
| 5,676,702 A | 10/1997 | Ratron |
| 5,683,465 A | 11/1997 | Shinn et al. |
| 5,702,450 A | 12/1997 | Bisserie |
| 5,709,683 A | 1/1998 | Bagby |
| 5,728,159 A | 3/1998 | Stroever et al. |
| 5,741,253 A | 4/1998 | Michelson |
| 5,776,198 A | 7/1998 | Rabbe et al. |
| 5,782,832 A | 7/1998 | Larsen et al. |
| 5,797,909 A | 8/1998 | Michelson |
| 5,824,094 A | 10/1998 | Serhan et al. |
| 5,865,846 A | 2/1999 | Bryan et al. |
| 5,865,848 A | 2/1999 | Baker |
| 5,888,226 A | 3/1999 | Rogozinski |
| 5,895,428 A | 4/1999 | Berry |
| 5,899,901 A | 5/1999 | Middleton |
| 5,899,911 A | 5/1999 | Carter |
| 5,928,284 A | 7/1999 | Mehdizadeh |
| 5,989,251 A | 11/1999 | Nichols |
| 5,989,291 A | 11/1999 | Ralph et al. |
| 6,001,130 A | 12/1999 | Bryan et al. |
| 6,019,792 A | 2/2000 | Cauthen |
| 6,022,376 A | 2/2000 | Assell et al. |
| 6,039,761 A | 3/2000 | Li et al. |
| 6,039,763 A | 3/2000 | Shelokov |
| 6,080,155 A | 6/2000 | Michelson |
| 6,083,228 A | 7/2000 | Michelson |
| 6,086,613 A | 7/2000 | Camino et al. |
| 6,096,038 A | 8/2000 | Michelson |
| 6,132,465 A | 10/2000 | Ray et al. |
| 6,136,031 A | 10/2000 | Middleton |
| 6,139,551 A | 10/2000 | Michelson et al. |
| 6,139,579 A | 10/2000 | Steffee et al. |
| 6,143,033 A | 11/2000 | Paul et al. |
| 6,146,421 A | 11/2000 | Gordon et al. |
| 6,156,067 A | 12/2000 | Bryan et al. |
| 6,159,214 A | 12/2000 | Michelson |
| 6,162,252 A | 12/2000 | Kuras et al. |
| 6,176,881 B1 | 1/2001 | Schar et al. |
| 6,193,757 B1 | 2/2001 | Foley et al. |
| 6,224,595 B1 | 5/2001 | Michelson |
| 6,231,609 B1 | 5/2001 | Mehdizadeh |
| 6,235,030 B1 | 5/2001 | Zucherman et al. |
| 6,261,296 B1 | 7/2001 | Aebi et al. |
| 6,264,695 B1 | 7/2001 | Stoy |
| 6,296,664 B1 | 10/2001 | Middleton |
| 6,315,797 B1 | 11/2001 | Middleton |
| 6,322,567 B1 | 11/2001 | Mittelstadt et al. |
| 6,336,941 B1 | 1/2002 | Subba Rao et al. |
| 6,348,071 B1 | 2/2002 | Steffee et al. |
| 6,368,350 B1 | 4/2002 | Erickson et al. |
| 6,368,351 B1 | 4/2002 | Glenn et al. |
| 6,375,681 B1 | 4/2002 | Truscott |
| 6,375,682 B1 | 4/2002 | Fleischmann et al. |
| 6,395,032 B1 | 5/2002 | Gauchet |
| 6,402,785 B1 | 6/2002 | Zdeblick et al. |
| 6,409,766 B1 | 6/2002 | Brett |
| 6,413,278 B1 | 7/2002 | Marchosky |
| 6,416,551 B1 | 7/2002 | Keller |
| 6,436,098 B1 | 8/2002 | Michelson |
| 6,440,139 B2 | 8/2002 | Michelson |
| 6,447,544 B1 | 9/2002 | Michelson |
| 6,478,800 B1 | 11/2002 | Fraser et al. |
| 6,517,544 B1 | 2/2003 | Michelson |
| 6,517,580 B1 | 2/2003 | Ramadan et al. |
| 6,520,967 B1 | 2/2003 | Cauthen |
| 6,520,996 B1 | 2/2003 | Manasas et al. |
| 6,527,804 B1 | 3/2003 | Gauchet et al. |
| 6,533,817 B1 | 3/2003 | Norton et al. |
| 6,537,279 B1 | 3/2003 | Michelson |
| 6,554,863 B2 | 4/2003 | Paul et al. |
| 6,562,047 B2 | 5/2003 | Ralph et al. |
| 6,562,074 B2 | 5/2003 | Gerbec et al. |
| 6,565,574 B2 | 5/2003 | Michelson |
| 6,582,466 B1 | 6/2003 | Gauchet |
| 6,582,468 B1 | 6/2003 | Gauchet |
| 6,592,624 B1 | 7/2003 | Fraser et al. |
| 6,599,294 B2 | 7/2003 | Fuss et al. |
| 6,607,558 B2 | 8/2003 | Kuras |
| 6,607,559 B2 | 8/2003 | Ralph et al. |
| 6,610,092 B2 | 8/2003 | Ralph et al. |
| 6,623,525 B2 | 9/2003 | Ralph et al. |
| 6,645,248 B2 | 11/2003 | Casutt |
| 6,648,895 B2 | 11/2003 | Burkus et al. |
| 6,652,533 B2 | 11/2003 | O'Neil |
| 6,660,038 B2 | 12/2003 | Boyer, II et al. |
| 6,666,866 B2 | 12/2003 | Martz et al. |
| 6,669,731 B2 | 12/2003 | Ralph et al. |
| 6,669,732 B2 | 12/2003 | Serhan et al. |
| 6,673,113 B2 | 1/2004 | Ralph et al. |
| 6,682,562 B2 | 1/2004 | Viart et al. |
| 6,689,132 B2 | 2/2004 | Biscup |
| 6,706,068 B2 | 3/2004 | Ferree |
| 6,709,439 B2 | 3/2004 | Rogers et al. |
| 6,712,819 B2 | 3/2004 | Zucherman et al. |
| 6,712,825 B2 | 3/2004 | Aebi et al. |
| 6,723,097 B2 | 4/2004 | Fraser et al. |
| 6,726,720 B2 | 4/2004 | Ross et al. |
| 6,726,721 B2 | 4/2004 | Stoy et al. |
| 6,733,532 B1 | 5/2004 | Gauchet et al. |
| 6,740,118 B2 | 5/2004 | Eisermann et al. |
| 6,740,119 B2 | 5/2004 | Ralph et al. |
| 6,755,841 B2 | 6/2004 | Fraser et al. |
| 6,764,515 B2 | 7/2004 | Ralph et al. |
| 6,770,095 B2 | 8/2004 | Grinberg et al. |
| 6,793,678 B2 | 9/2004 | Hawkins |
| 6,814,737 B2 | 11/2004 | Cauthen |
| 6,821,298 B1 | 11/2004 | Jackson |
| 6,827,740 B1 | 12/2004 | Michelson |
| 6,846,328 B2 | 1/2005 | Cauthen |
| 6,875,213 B2 | 4/2005 | Michelson |
| 6,896,680 B2 | 5/2005 | Michelson |
| 6,936,132 B2 | 8/2005 | Topolnitsky |
| 6,963,071 B2 | 11/2005 | Bristol |
| 6,964,686 B2 | 11/2005 | Gordon |
| 6,966,929 B2 | 11/2005 | Mitchell |
| 6,989,011 B2 | 1/2006 | Paul et al. |
| 6,994,727 B2 | 2/2006 | Khandkar et al. |
| 7,011,684 B2 | 3/2006 | Eckman |
| 7,022,138 B2 | 4/2006 | Mashburn |
| 7,025,787 B2 | 4/2006 | Bryan et al. |
| 7,044,983 B1 | 5/2006 | Cheng |
| 7,056,344 B2 | 6/2006 | Huppert et al. |
| 7,060,073 B2 | 6/2006 | Frey et al. |
| 7,066,958 B2 | 6/2006 | Ferree |
| 7,081,120 B2 | 7/2006 | Li et al. |

(56) References Cited

U.S. PATENT DOCUMENTS

| | | |
|---|---|---|
| 7,083,651 B2 | 8/2006 | Diaz et al. |
| 7,087,055 B2 | 8/2006 | Lim et al. |
| 7,097,648 B1 | 8/2006 | Globerman et al. |
| 7,118,580 B1 | 10/2006 | Beyersdorff et al. |
| 7,147,665 B1 | 12/2006 | Bryan et al. |
| 7,153,325 B2 | 12/2006 | Kim et al. |
| 7,179,294 B2 | 2/2007 | Eisermann et al. |
| 7,182,784 B2 | 2/2007 | Evans et al. |
| 7,207,991 B2 | 4/2007 | Michelson |
| 7,214,244 B2 | 5/2007 | Zubok et al. |
| 7,217,291 B2 | 5/2007 | Zucherman et al. |
| 7,235,103 B2 | 6/2007 | Rivin |
| 7,250,060 B2 | 7/2007 | Trieu |
| 7,255,714 B2 | 8/2007 | Malek |
| 7,261,739 B2 | 8/2007 | Ralph et al. |
| 7,267,688 B2 | 9/2007 | Ferree |
| 7,270,679 B2 | 9/2007 | Istephanous et al. |
| 7,318,839 B2 | 1/2008 | Malberg et al. |
| 7,331,995 B2 | 2/2008 | Eisermann et al. |
| 7,442,211 B2 | 10/2008 | de Villiers et al. |
| 7,452,380 B2 | 11/2008 | Zubok et al. |
| 2001/0016773 A1 | 8/2001 | Serhan et al. |
| 2001/0029377 A1 | 10/2001 | Aebi et al. |
| 2002/0022845 A1 | 2/2002 | Zdeblick et al. |
| 2002/0035400 A1 | 3/2002 | Bryan et al. |
| 2002/0045904 A1 | 4/2002 | Fuss et al. |
| 2002/0068936 A1 | 6/2002 | Burkus et al. |
| 2002/0091392 A1 | 7/2002 | Michelson |
| 2002/0116009 A1 | 8/2002 | Fraser et al. |
| 2002/0123753 A1 | 9/2002 | Michelson |
| 2002/0128715 A1 | 9/2002 | Bryan et al. |
| 2002/0165550 A1 | 11/2002 | Frey et al. |
| 2002/0177897 A1 | 11/2002 | Michelson |
| 2002/0198532 A1 | 12/2002 | Michelson |
| 2003/0009224 A1 | 1/2003 | Kuras |
| 2003/0023245 A1 | 1/2003 | Ralph et al. |
| 2003/0028249 A1 | 2/2003 | Baccelli et al. |
| 2003/0045884 A1 | 3/2003 | Robie et al. |
| 2003/0045939 A1 | 3/2003 | Casutt |
| 2003/0074076 A1 | 4/2003 | Ferree |
| 2003/0100951 A1 | 5/2003 | Serhan et al. |
| 2003/0125739 A1 | 7/2003 | Bagga |
| 2003/0130662 A1 | 7/2003 | Michelson |
| 2003/0135277 A1 | 7/2003 | Bryan et al. |
| 2003/0187448 A1 | 10/2003 | Michelson |
| 2003/0191536 A1 | 10/2003 | Ferree |
| 2003/0195517 A1 | 10/2003 | Michelson |
| 2003/0195631 A1 | 10/2003 | Ferree |
| 2003/0199982 A1 | 10/2003 | Bryan |
| 2003/0204261 A1 | 10/2003 | Eisermann et al. |
| 2003/0208271 A1 | 11/2003 | Kuras |
| 2003/0229358 A1 | 12/2003 | Errico et al. |
| 2004/0002761 A1 | 1/2004 | Rogers et al. |
| 2004/0024407 A1 | 2/2004 | Ralph |
| 2004/0024410 A1 | 2/2004 | Olson et al. |
| 2004/0030391 A1 | 2/2004 | Ferree |
| 2004/0034426 A1 | 2/2004 | Errico et al. |
| 2004/0054411 A1 | 3/2004 | Kelly et al. |
| 2004/0059318 A1 | 3/2004 | Zhang et al. |
| 2004/0073307 A1 | 4/2004 | Keller |
| 2004/0073312 A1 | 4/2004 | Eisermann et al. |
| 2004/0093087 A1 | 5/2004 | Ferree et al. |
| 2004/0097928 A1 | 5/2004 | Zdeblick et al. |
| 2004/0098131 A1 | 5/2004 | Bryan et al. |
| 2004/0143270 A1 | 7/2004 | Zucherman et al. |
| 2004/0143332 A1 | 7/2004 | Krueger et al. |
| 2004/0143334 A1 | 7/2004 | Ferree |
| 2004/0167626 A1 | 8/2004 | Geremakis et al. |
| 2004/0176843 A1 | 9/2004 | Zubok et al. |
| 2004/0186569 A1 | 9/2004 | Berry |
| 2004/0215342 A1 | 10/2004 | Suddaby |
| 2004/0225295 A1 | 11/2004 | Zubok et al. |
| 2004/0225365 A1 | 11/2004 | Eisermann et al. |
| 2004/0236426 A1 | 11/2004 | Ralph et al. |
| 2004/0254644 A1 | 12/2004 | Taylor |
| 2005/0015094 A1 | 1/2005 | Keller |
| 2005/0015095 A1 | 1/2005 | Keller |
| 2005/0021145 A1 | 1/2005 | de Villiers et al. |
| 2005/0021146 A1 | 1/2005 | de Villiers et al. |
| 2005/0027360 A1 | 2/2005 | Webb et al. |
| 2005/0038515 A1 | 2/2005 | Kunzler |
| 2005/0043800 A1 | 2/2005 | Paul et al. |
| 2005/0055029 A1* | 3/2005 | Marik et al. .................. 606/87 |
| 2005/0085917 A1 | 4/2005 | Marnay et al. |
| 2005/0107881 A1 | 5/2005 | Alleyne et al. |
| 2005/0113842 A1 | 5/2005 | Bertagnoli et al. |
| 2005/0113928 A1 | 5/2005 | Cragg |
| 2005/0149189 A1 | 7/2005 | Mokhtar et al. |
| 2005/0154463 A1 | 7/2005 | Trieu |
| 2005/0165408 A1 | 7/2005 | Puno et al. |
| 2005/0192586 A1 | 9/2005 | Zucherman et al. |
| 2005/0192670 A1 | 9/2005 | Zubok et al. |
| 2005/0197706 A1 | 9/2005 | Hovorka et al. |
| 2005/0216081 A1 | 9/2005 | Taylor |
| 2005/0216084 A1 | 9/2005 | Fleischmann et al. |
| 2005/0234553 A1 | 10/2005 | Gordon |
| 2005/0251260 A1 | 11/2005 | Gerber et al. |
| 2005/0251261 A1 | 11/2005 | Peterman |
| 2005/0251262 A1 | 11/2005 | de Villiers et al. |
| 2005/0261772 A1 | 11/2005 | Filippi et al. |
| 2005/0267580 A1 | 12/2005 | Suddaby |
| 2005/0267581 A1 | 12/2005 | Marnay et al. |
| 2006/0004377 A1 | 1/2006 | Keller |
| 2006/0004453 A1 | 1/2006 | Bartish et al. |
| 2006/0015183 A1 | 1/2006 | Gilbert et al. |
| 2006/0020342 A1 | 1/2006 | Ferree et al. |
| 2006/0025862 A1 | 2/2006 | de Villiers et al. |
| 2006/0029186 A1 | 2/2006 | de Villiers et al. |
| 2006/0030857 A1 | 2/2006 | de Villiers et al. |
| 2006/0030862 A1 | 2/2006 | de Villiers et al. |
| 2006/0036325 A1 | 2/2006 | Paul et al. |
| 2006/0041313 A1 | 2/2006 | Allard et al. |
| 2006/0041314 A1 | 2/2006 | Millard |
| 2006/0069439 A1 | 3/2006 | Zucherman et al. |
| 2006/0116768 A1* | 6/2006 | Krueger et al. .............. 623/17.14 |
| 2006/0142858 A1 | 6/2006 | Colleran |
| 2006/0142862 A1 | 6/2006 | Diaz et al. |
| 2006/0155378 A1 | 7/2006 | Eckman |
| 2006/0167549 A1 | 7/2006 | Mathys et al. |
| 2006/0178744 A1 | 8/2006 | de Villiers et al. |
| 2006/0178746 A1 | 8/2006 | Bartish, Jr. et al. |
| 2006/0190084 A1* | 8/2006 | Doubler et al. ............. 623/17.14 |
| 2006/0195097 A1 | 8/2006 | Evans et al. |
| 2006/0200239 A1 | 9/2006 | Rothman et al. |
| 2006/0224241 A1 | 10/2006 | Butler et al. |
| 2006/0235426 A1 | 10/2006 | Lim et al. |
| 2006/0235525 A1 | 10/2006 | Gil et al. |
| 2006/0235527 A1 | 10/2006 | Buettner-Janz et al. |
| 2006/0241641 A1 | 10/2006 | Albans et al. |
| 2006/0259144 A1 | 11/2006 | Trieu |
| 2006/0259146 A1 | 11/2006 | Navarro et al. |
| 2006/0265068 A1 | 11/2006 | Schwab |
| 2006/0293752 A1 | 12/2006 | Moumene et al. |
| 2006/0293754 A1 | 12/2006 | de Villiers et al. |
| 2007/0010826 A1 | 1/2007 | Rhoda et al. |
| 2007/0032875 A1 | 2/2007 | Blacklock et al. |
| 2007/0061011 A1 | 3/2007 | de Villiers et al. |
| 2007/0067035 A1 | 3/2007 | Falahee |
| 2007/0073398 A1 | 3/2007 | Fabian et al. |
| 2007/0100453 A1 | 5/2007 | Parsons et al. |
| 2007/0100454 A1 | 5/2007 | Burgess et al. |
| 2007/0100456 A1 | 5/2007 | Dooris et al. |
| 2007/0123903 A1 | 5/2007 | Raymond et al. |
| 2007/0123904 A1 | 5/2007 | Stad et al. |
| 2007/0135923 A1 | 6/2007 | Peterman et al. |
| 2007/0168033 A1 | 7/2007 | Kim et al. |
| 2007/0168036 A1 | 7/2007 | Ainsworth et al. |
| 2007/0213821 A1 | 9/2007 | Kwak et al. |
| 2007/0233077 A1 | 10/2007 | Khalili |
| 2007/0233251 A1 | 10/2007 | Abdou |
| 2007/0282449 A1 | 12/2007 | de Villiers et al. |
| 2008/0015698 A1 | 1/2008 | Marino et al. |
| 2008/0015701 A1 | 1/2008 | Garcia et al. |
| 2008/0021557 A1 | 1/2008 | Trieu |

(56) References Cited

U.S. PATENT DOCUMENTS

| | | | |
|---|---|---|---|
| 2008/0051900 A1 | 2/2008 | de Villiers et al. | |
| 2008/0051901 A1 | 2/2008 | de Villiers et al. | |
| 2008/0114453 A1* | 5/2008 | Francis | 623/17.14 |
| 2008/0125864 A1 | 5/2008 | de Villiers et al. | |
| 2008/0133011 A1 | 6/2008 | de Villiers et al. | |
| 2008/0154301 A1 | 6/2008 | de Villiers et al. | |
| 2008/0154382 A1 | 6/2008 | de Villiers et al. | |
| 2008/0215155 A1 | 9/2008 | de Villiers et al. | |
| 2008/0221696 A1 | 9/2008 | de Villiers et al. | |
| 2008/0228274 A1 | 9/2008 | de Villiers et al. | |
| 2008/0228277 A1 | 9/2008 | de Villiers et al. | |
| 2008/0294259 A1 | 11/2008 | de Villiers et al. | |
| 2009/0043391 A1 | 2/2009 | de Villiers et al. | |
| 2009/0048674 A1 | 2/2009 | Zubok et al. | |
| 2009/0076614 A1 | 3/2009 | Arramon | |
| 2009/0088850 A1* | 4/2009 | Froehlich | 623/17.16 |
| 2009/0105833 A1 | 4/2009 | Hovda et al. | |
| 2009/0105834 A1 | 4/2009 | Hovda et al. | |
| 2009/0105835 A1 | 4/2009 | Hovda et al. | |

FOREIGN PATENT DOCUMENTS

| | | |
|---|---|---|
| EP | 0 560 140 | 9/1993 |
| EP | 0 560 141 | 9/1993 |
| EP | 0 591 712 | 4/1994 |
| EP | 0 820 740 | 1/1998 |
| EP | 1 142 544 | 10/2001 |
| EP | 1 153 582 | 11/2001 |
| EP | 1 250 898 | 10/2002 |
| EP | 1 306 064 | 5/2003 |
| EP | 1 344 493 | 9/2003 |
| EP | 1 344 506 | 9/2003 |
| EP | 1 344 507 | 9/2003 |
| EP | 1 344 508 | 9/2003 |
| EP | 1 417 940 | 5/2004 |
| EP | 1 570 813 | 9/2005 |
| FR | 2 803 741 | 7/2001 |
| WO | 99/20209 | 4/1999 |
| WO | 99/30651 | 6/1999 |
| WO | 00/35384 | 6/2000 |
| WO | 00/42954 | 7/2000 |
| WO | 01/01893 | 1/2001 |
| WO | 2004/000170 | 12/2003 |
| WO | 2004/000171 | 12/2003 |
| WO | 2004/026187 | 4/2004 |
| WO | 2005/053580 | 6/2005 |
| WO | 2005/072662 | 8/2005 |
| ZA | 03/9312 | 11/2003 |

OTHER PUBLICATIONS

Buttner-Janz, "The Development of the Artificial Disc," Introduction, pp. 1-18, Library of Congress Catalogue No. 92-75582, ISBN 0-9635430-0-8 (1989).

Hellier et al., "Wear Studies for Development of an Intervertebral Disc Prosthesis," *Spine*, vol. 17 No. 6 Supplement pp. 86-96 (1992).

Lee et al., "Impact Response of the Intervertebral Disc in a Finite-Element Model," *Spine* vol. 25, No. 19, pp. 2431-2439 (2000).

Lehuec et al., "Shock Absorption in Lumber Disc Prosthesis," *Journal of Spinal Disorders & Techniques*, vol. 16, No. 4, pp. 346-351 (2003).

* cited by examiner

ARTIFICIAL INTERVERTEBRAL DISC WITH LOWER HEIGHT

CROSS-REFERENCES TO RELATED APPLICATIONS

This application claims priority to U.S. Provisional Application No. 61/069,048, filed Mar. 11, 2008, entitled "ARTIFICIAL INTERVERTEBRAL DISC WITH LOWER HEIGHT" the full disclosure of which is incorporated herein by reference.

BACKGROUND OF THE INVENTION

The present invention relates to medical devices and methods. More specifically, the present invention relates to intervertebral disc prostheses.

Back pain takes an enormous toll on the health and productivity of people around the world. According to the American Academy of Orthopedic Surgeons, approximately 80 percent of Americans will experience back pain at some time in their life. On any one day, it is estimated that 5% of the working population in America is disabled by back pain.

One common cause of back pain is injury, degeneration and/or dysfunction of one or more intervertebral discs. Intervertebral discs are the soft tissue structures located between each of the thirty-three vertebral bones that make up the vertebral (spinal) column. Essentially, the discs allow the vertebrae to move relative to one another. The vertebral column and discs are vital anatomical structures, in that they form a central axis that supports the head and torso, allow for movement of the back, and protect the spinal cord, which passes through the vertebrae in proximity to the discs.

Discs often become damaged due to wear and tear or acute injury. For example, discs may bulge (herniate), tear, rupture, degenerate or the like. A bulging disc may press against the spinal cord or a nerve exiting the spinal cord, causing "radicular" pain (pain in one or more extremities caused by impingement of a nerve root). Degeneration or other damage to a disc may cause a loss of "disc height," meaning that the natural space between two vertebrae decreases. Decreased disc height may cause a disc to bulge, facet loads to increase, two vertebrae to rub together in an unnatural way and/or increased pressure on certain parts of the vertebrae and/or nerve roots, thus causing pain. In general, chronic and acute damage to intervertebral discs is a common source of back related pain and loss of mobility.

When one or more damaged intervertebral discs cause a patient pain and discomfort, surgery is often required. Traditionally, surgical procedures for treating intervertebral discs have involved discectomy (partial or total removal of a disc), with or without fusion of the two vertebrae adjacent to the disc. Fusion of the two vertebrae is achieved by inserting bone graft material between the two vertebrae such that the two vertebrae and the graft material grow together. Oftentimes, pins, rods, screws, cages and/or the like are inserted between the vertebrae to act as support structures to hold the vertebrae and graft material in place while they permanently fuse together. Although fusion often treats the back pain, it reduces the patient's ability to move, because the back cannot bend or twist at the fused area. In addition, fusion increases stresses at adjacent levels of the spine, potentially accelerating degeneration of these discs.

In an attempt to treat disc related pain without fusion, an alternative approach has been developed, in which a movable, implantable, artificial intervertebral disc (or "disc prosthesis") is inserted between two vertebrae. A number of different artificial intervertebral discs are currently being developed. For example, U.S. Patent Application Publication Nos. 2005-0021146, 2005-0021145, and 2006-0025862, which are hereby incorporated by reference in their entirety, describe artificial intervertebral discs. This type of intervertebral disc has upper and lower plates positioned against the vertebrae and a mobile core positioned between two plates to allow articulating, lateral and rotational motion between the vertebrae.

Another example of an intervertebral disc prostheses having a movable core is the CHARITE artificial disc (provided by DePuy Spine, Inc.) and described in U.S. Pat. No. 5,401,269. Other examples of intervertebral disc prostheses include MOBIDISC (provided by LDR Medical), the BRYAN Cervical Disc (provided by Medtronic Sofamor Danek, Inc.), and the PRODISC (from Synthes Stratec, Inc.) and described in U.S. Pat. No. 6,936,071. Some of these intervertebral discs are mobile core discs while others have a ball and socket type two piece design. Although existing disc prostheses provide advantages over traditional treatment methods, improvements are ongoing.

These known artificial intervertebral discs generally include upper and lower plates which locate against and engage the adjacent vertebral bodies, and a core for providing motion between the plates. The core may be movable or fixed, metallic, ceramic or polymer and generally has at least one convex outer surface which mates with a concave recess on one of the plates in a fixed core device or both of the plates for a movable core device. In order to implant these intervertebral discs, the natural disc is removed and the vertebrae are distracted or forced apart in order to fit the artificial disc in place. Depending on the size of the disc space, many of the known artificial discs have a height which is higher than desired resulting in an unnaturally over distracted condition upon implantation of the disc. For example, a smallest height disc available can be about 10-13 mm for lumbar discs and about 5-6 mm for cervical discs.

Currently available artificial intervertebral discs do not provide a desired low profile for some patients with smaller disc heights. The use of an artificial disc which is too large for a patient's disc space can result in limited mobility of the disc. An improperly sized artificial disc can also move out of place in the disc space. Accordingly, it would be desirable to provide a lower height disc which mimics more closely the natural anatomy for smaller patients.

In addition, the vertebral body contacting surfaces of many of the known artificial discs are flat. This flat configuration does not generally match the surfaces of the vertebral bodies resulting in less than ideal bone to implant contact surfaces. It would be desirable to provide a more anatomically shaped vertebral body contacting surface for an artificial disc.

Therefore, a need exists for an improved artificial intervertebral disc with a lower disc height and more anatomically shaped upper surface.

BRIEF SUMMARY OF THE INVENTION

According to the invention there is provided an intervertebral prosthesis for insertion between adjacent vertebrae, the prosthesis comprising upper and lower prosthesis plates with domed outer surfaces locatable against adjacent vertebral bodies.

In accordance with another aspect of the invention, an intervertebral disc includes an upper plate having an upper vertebra contacting surface and a lower bearing surface and a lower plate having a lower vertebra contacting surface and an upper surface. The upper surface of the upper plate has a convex central portion and at least one anchoring element extending from an upper surface of the convex central portion. The lower bearing surface of the upper plate has a concavity disposed opposite the convex central portion. The lower surface of the lower plate has a convex central portion and the upper bearing surface of the lower plate has a concavity disposed opposite the convex central portion. A core is positioned between the upper and lower plates, the core having upper and lower convex surfaces configured to mate with the bearing surfaces of the upper and lower plates.

In accordance with a further aspect of the invention, an intervertebral disc includes a first plate having a first vertebrae contacting surface and a bearing surface opposite the first vertebrae contacting surface, and a second plate having a second vertebrae contacting surface and an opposite surface and wherein the second plate articulates with respect to the first plate. The first vertebrae contacting surface of the first plate has a convex central dome shaped portion and at least one anchoring fin extending from an outer surface of the convex central dome shaped portion, and the bearing surface of the first plate has a concavity directly opposed to the convex central portion.

In accordance with an additional aspect of the invention, an intervertebral disc includes an upper plate having an upper vertebra contacting surface and a lower surface, and a lower plate having a lower vertebra contacting surface and an upper surface, and the upper plate articulates with respect to the lower plate. The upper surface of the upper plate has at least one anchoring fin extending from the upper surface of the upper plate and the lower surface of the lower plate has at least one anchoring fin extending from the lower surface of the lower plate. A plurality of teeth are positioned in a symmetrical pattern on opposite sides of the anchoring fins of the upper and lower plates, the plurality of teeth each having a first surface and a second surface opposite the first surface, wherein the first surface is formed at an angle of less than 40 degrees with respect to the vertebra contacting surfaces and the second surface is formed at an angle of more than 50 degrees with respect to the vertebra contacting surfaces. A plurality of serrations surround the plurality of teeth, wherein the plurality of serrations have a height at least 25 percent lower than a height of the teeth.

Other features of the invention are set forth in the appended claims.

DETAILED DESCRIPTION OF THE INVENTION

Figure 1:
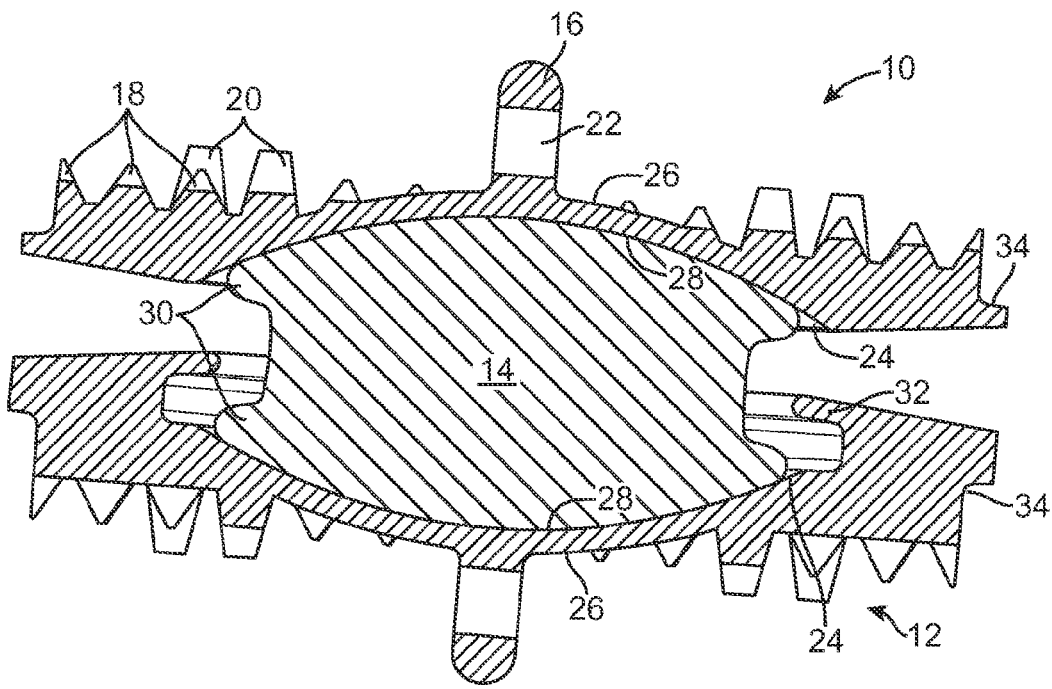
FIG. 1 is a cross sectional view of an intervertebral disc according to one embodiment of the present invention.
Figure 2:
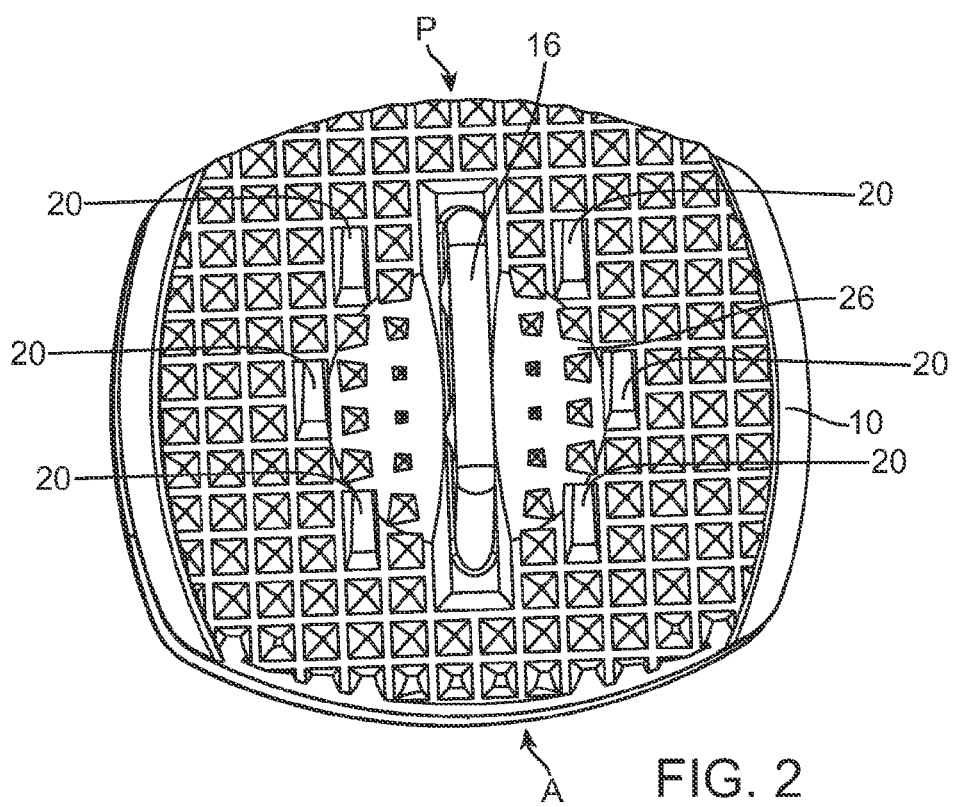
FIG. 2 is a top view of the intervertebral disc of FIG. 1.
Figure 3:
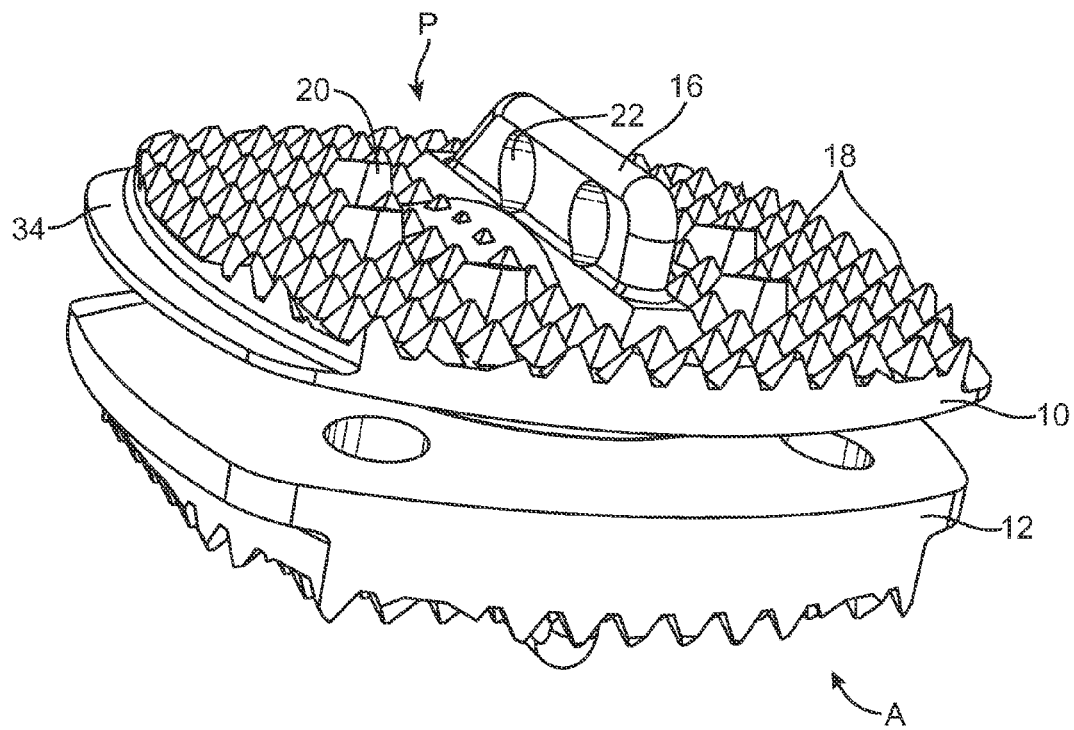
FIG. 3 is a perspective view of the intervertebral disc of FIG. 1.

FIGS. 1-3 illustrate an intervertebral disc having an upper plate 10, a lower plate 12, and a core 14. The upper and lower plates 10, 12 include outer vertebral body contacting surfaces which are provided with attachment enhancing features to ensure bone integration. The attachment enhancing features shown include one or more fins 16, serrations 18 and teeth 20.

The fin 16 can be an elongate fin pierced by one or more transverse holes 22. The disc can be inserted posteriorly into the patient from an anterior access, such that fin 16 can enter a groove in one of the vertebrae as a posterior side P of the intervertebral disc enters the intervertebral space followed by an anterior side A of the intervertebral disc. An opposite surface of the plates from the vertebral body contacting surfaces is formed with a recess 24 which serves as a bearing surface for the core 14. In order to form an intervertebral disc with a lower disc height, at least one of the recesses 24 is provided opposite a corresponding dome shaped portion 26 on the vertebral body contacting surfaces. This allows the plates 10, 12 to be formed with a thinner profile for a smaller overall disc height.

In addition to providing a lower overall height to the artificial disc, the dome shaped portion 26 of the plates also provides a more anatomically shaped outer vertebral body contacting surface. The surfaces of the vertebral bodies are commonly not flat, but instead have a slight dish shape to their center portion. The dome shaped portion 26 fits well into this dish shape of the vertebrae providing better bone contact and improved bone integration.

The core 14 can be formed as a circular disc shaped member with upper and lower bearing surfaces 28 which match the curvature of the recesses 24. The core 14 also has an annular rim 30 which cooperates with a retention feature 32 on at least one of the discs to retain the core between the plates when the intervertebral disc is implanted between the vertebrae of a patient. The core 14 is moveable with respect to both the upper and lower discs to allow articulation, translation and rotation of the upper and lower plates with respect to one another. The core surfaces 28 and recess surface 24 have the same radius of curvature which may vary depending on the size of the intervertebral disc.

In the embodiment shown in FIGS. 1-3 a single central fin 16 is provided on each of the plates 10, 12 extending in an anterior posterior direction with an angled posterior edge for aiding in insertion. This embodiment is particularly useful for insertion from an anterior side of the intervertebral disc space. Alternatively, two or more fins 16 can also be provided on each plate. In one example, a single fin can be provided on one plate while double fins can be symmetrically arranged on the other plate to achieve a staggered arrangement particularly useful for multi-level disc implant procedures. This staggered arrangement prevents the rare occurrence of vertebral body splitting by avoiding cuts to the vertebral body in the same plane for multi-level implants. The orientation of the fin(s) 16 can also be modified depending on the insertion direction for the intervertebral disc 10. In alternative embodiments, the fins 16 may be rotated away from the anterior-posterior axis, such as in a lateral-lateral orientation, a posterolateral-anterolateral orientation, or the like for implantation in the associated directions.

The fins 16 are configured to be placed in slots in the vertebral bodies. In one embodiment, the fins 16 are pierced by transverse holes 54 for bone ingrowth. The transverse holes 54 may be formed in any shape and may extend partially or all the way through the fins 50, 52. Preferably, the fins 16 each have a height greater than a width and have a length greater than the height.

The fins 16 provide improved attachment to the bone and prevent rotation of the plates in the bone. In some embodiments, the fins 16 may extend from the surface of the plates 10, 12 at an angle other than 90°. For example on one or more of the plates 10, 12 where multiple fins 16 are attached to the surface the fins may be canted away from one another with the bases slightly closer together than their edges at an angle such as about 80-88 degrees. The fins 16 may have any other suitable configuration including various numbers angles and curvatures, in various embodiments. In some embodiments, the fins 16 may be omitted altogether.

Figure 4:
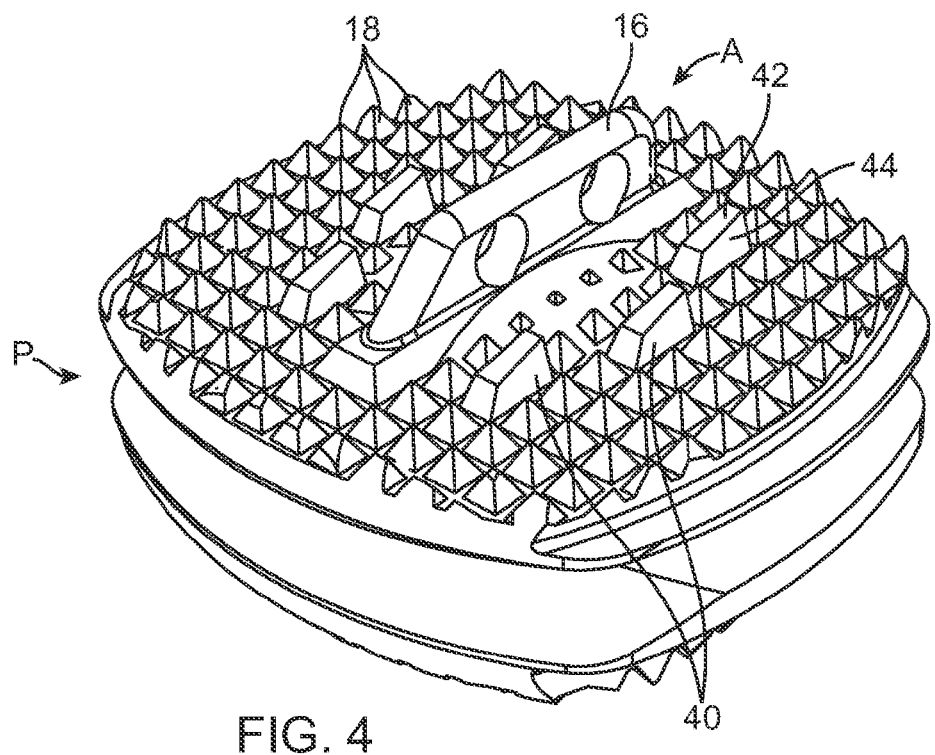
FIG. 4 is a perspective view of an intervertebral disc according to another embodiment of the invention.

The teeth 20 shown in FIG. 1 to FIG. 3 include six teeth arranged in a chevron shape with the narrow portion of the chevron located on a posterior side of the plates 10, 12. However, other numbers of teeth and teeth arrangements may also be used. For example, the teeth 20 may be arranged, as shown in FIG. 4, in an alternating arrangement such that the first and third teeth on each side are aligned and located closer to the midline of the disc while the central tooth is located further from the midline (a diamond shape pattern). The teeth can be positioned in varying numbers and arrangements depending on the size and shape of the plate used.

Figure 2A:
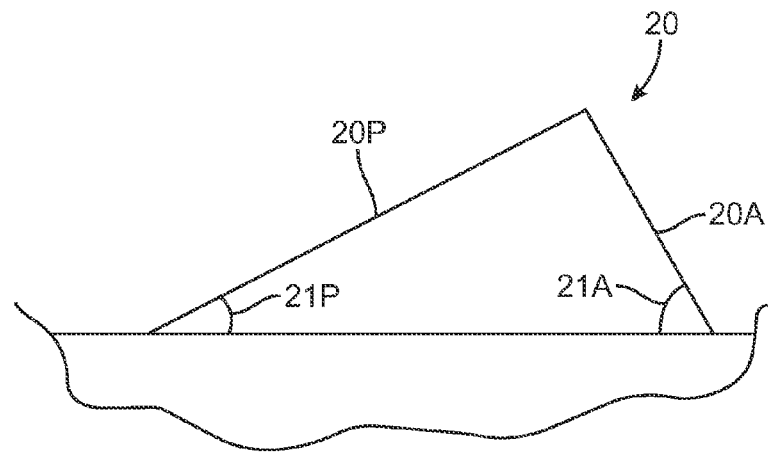
FIG. 2A is a side profile view of the teeth shown in FIG. 1.

The teeth 20 as shown in FIG. 1 to FIG. 3 have an elongated shape with opposite triangular side surfaces. As shown most clearly in FIG. 2A, each of teeth 20 comprises a posterior surface 20P and anterior surface 20A. In the embodiment of FIGS. 1-3, the teeth each have posterior surface 20P opposite anterior surface 20A, wherein the posterior surface is formed at an angle 21P of less than 40 degrees with respect to the vertebra contacting surfaces of the plates 10, 12, and the anterior surface 20A is formed at an angle 21A of more than 50 degrees with respect to the vertebra contacting surfaces. Preferably, the posterior surface 21P is formed at an angle of about 5 to about 30 degrees, while the anterior surface 21A is formed at an angle of about 70 to about 90 degrees. In addition, the anterior surface 21A can be canted in the anterior direction to provide a tooth in the form of a barb. In this way, the posterior surface 21P provides minimal resistance to insertion while the anterior surface 21A prevents backing out of the disc.

Although wedge shaped teeth are shown, other teeth shapes may also be used, for example pyramidal, conical, rectangular and/or cylindrical teeth.

Referring now to FIG. 4, vertebrae contacting surfaces may comprise finlets 40. Finlets 40 can be somewhat larger than teeth and differ from teeth in that they have an additional top surface. The finlets 40 may have a tapered top surface 42 and larger base portion 44. The teeth 20 and/or finlets 40 may have a height which is preferably greater than that of the serrations. The teeth and/or finlet heights can be about 0.5-3 mm, preferably about 1-2 mm and more preferably about 1.1-1.5 mm. In the example of FIG. 4, the finlets 40 have an anterior surface formed at an angle of about 70 to 90 degrees, preferably about 80 degrees a posterior surface formed at an angle of about 50-70 degrees, preferably about 60 degrees, and a top surface formed at an angle of about 2-20 degrees, each with respect to the vertebra contacting surfaces.

The dome shaped portion(s) 26 on the vertebral body contacting surfaces are provided to allow the core 14 to be recessed further into the upper and lower plates 10, 12. The dome shaped portion preferably has a diameter less than a diameter of the core, i.e. less than about 20 mm for a lumbar disc and less than about 10 mm for a cervical disc. In one preferred embodiment, the external dome 26 has a diameter of about 10-20 mm for lumbar and about 5-10 mm for cervical. The dome in one embodiment has a height of about 0.5-3 mm above a plane formed by the vertebral body contacting surfaces of the plates at the base of the serrations, when serrations are present. Preferably, the dome height is about 0.7-2 mm.

In the embodiment shown in FIGS. 1-3, some of the serrations 18 are located on the surface of the dome shaped portion 26, with the tops of the serrations even with the serrations which are not positioned on the dome. Alternatively, the serrations 18 on the dome 26 can extend somewhat higher than the other serrations on the plates or serrations can be omitted on the dome shaped portion. The serrations 18 as shown are pyramid shaped serrations extending in mutually orthogonal directions, however, other shapes may also be used. The serrations have a height of about 0.5-1 mm and a width about equal to their height. With passage of time, firm connection between the plates 10, 12 and the vertebrae will be achieved as bone tissue grows over the serrated finish. Bone tissue growth will also take place about the fins 16 and through the holes 22 therein, further enhancing the connection which is achieved.

Other geometries of bone integration structures may also be used including teeth, grooves, ridges, pins, barbs or the like. When the bone integration structures are ridges, teeth, barbs or similar structures, they may be angled to ease insertion and prevent migration. These bone integration structures can be used to precisely cut the bone during implantation to cause bleeding bone and encourage bone integration. Additionally, the outer surfaces of the plates 10, 12 may be provided with a rough microfinish formed by blasting with aluminum oxide microparticles or the like to improve bone integration. In some embodiments, the outer surface may also be titanium plasma sprayed or HA coated to further enhance attachment of the outer surface to vertebral bone.

The core 14 according to the embodiments of FIGS. 1-4 can be retained in the lower plate 12 by retention feature 28 comprising a retention ring that protrudes inwardly from an edge of the lower plate 12 at an edge of the lower bearing surface 32 of the plate. Although a circumferential core retaining feature is shown, other core retaining features may also be used including at least those shown in U.S. Patent Publication Nos. 2005/0251262, 2005/0021146, and 2005/0021145, which are incorporated herein by reference in their entirety.

Although the core 14 has been shown as circular in cross section with spherically shaped bearing surfaces 28, other bearing surface shapes may be used including oval, elliptical, or kidney bean shaped. These non-circular shaped cores can be used to limit rotational motion between the upper and lower plates 10, 12. The bearing surface shapes may also vary from the spherical shapes shown and may vary between the upper and lower surfaces of the core. Other bearing surface shapes include cylindrical, elliptical, trough shaped, groves, flat surfaces, or the like. Although the core 14 and plates 10, 12 have been shown as solid members, the core and plates may be made in multiple parts and/or of multiple materials. The core can be made of low friction materials, such as titanium, titanium nitrides, other titanium based alloys, tantalum, nickel titanium alloys, stainless steel, cobalt chrome alloys, ceramics, or biologically compatible polymer materials including PEEK, UHMWPE, PLA or fiber reinforced polymers. High friction coating materials can also be used.

The intervertebral disc according to the present invention provides articulation in two directions as well as rotation. The plates 10, 12 are provided with grooves 34 at their lateral edges for use in grasping the disc by an instrument to facilitate holding and manipulation of the disc for insertion or removal of the disc. The grooves 34 allow the plates 10, 12 to be grasped and inserted simultaneously in a locked orientation.

The upper and lower plates 10, 12 may be formed from titanium, titanium nitrides, other titanium based alloys, tantalum, nickel titanium alloys, stainless steel, cobalt chrome alloys, ceramics, or biologically compatible polymer materials including PEEK, UHMWPE, PLA or fiber reinforced polymers. The bearing surfaces or recesses 24 are concavely, spherically curved and can have a hard coating such as a titanium nitride finish. The plates 10, 12 may be treated with aluminum oxide blasting followed by a titanium plasma spray to improve bone integration. Other materials and coatings can also be used such as titanium coated with titanium nitride, aluminum oxide blasting, HA (hydroxylapatite) coating, micro HA coating, and/or bone integration promoting coatings. Any other suitable metals or combinations of metals may be used as well as ceramic or polymer materials, and combinations thereof to optimize imaging characteristics. Any suitable technique may be used to couple materials together, such as snap fitting, slip fitting, lamination, interference fitting, use of adhesives, welding and/or the like.

Figure 5:
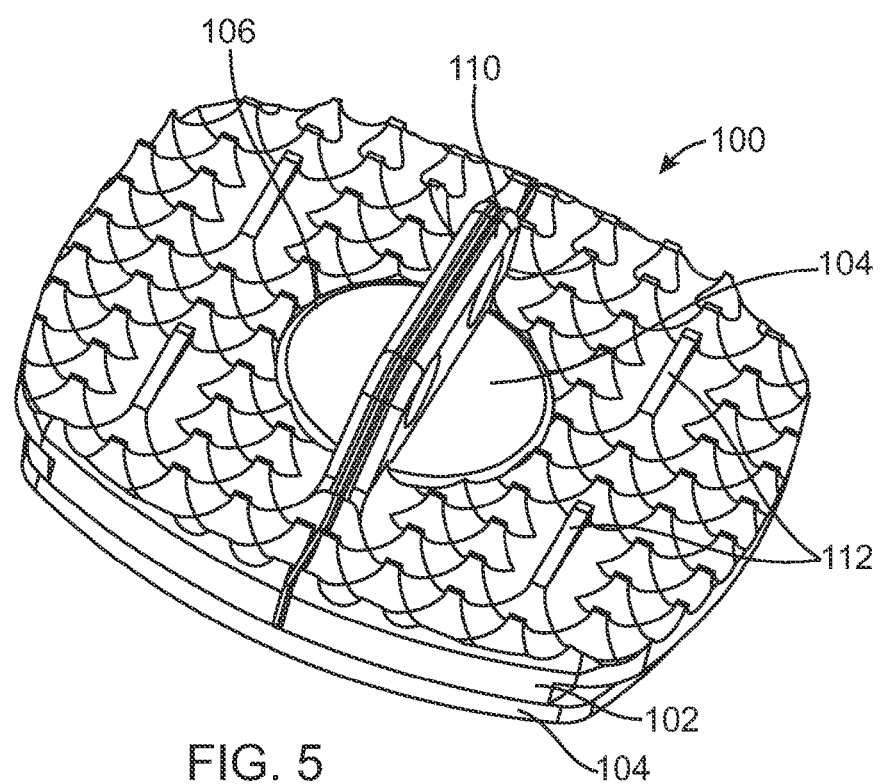
FIG. 5 is a perspective view of an intervertebral disc plate according to another embodiment of the invention with a bearing surface insert.

FIG. 5 illustrates an alternative embodiment of an intervertebral disc plate 100 having a metallic vertebral body contacting portion 102 and a bearing surface insert 104 formed of PEEK or other MRI compatible material. The PEEK insert 104 includes the bearing surface (not shown) and has a dome shaped central portion. The metallic portion 102 includes a central circular opening 106 which can be of any shape and accommodates a portion of the PEEK insert 104. The metallic portion 102 may be formed in two parts and welded around the PEEK insert 104 to form a firm connection between the metallic and PEEK portions of the plate. The PEEK insert provides the advantage of MRI compatibility while the metallic vertebral body contacting portion 102 provides a superior surface for bone integration and includes one or more fins 110, finlets 112, and serrations 114 as described with respect to the other embodiments described herein.

Each of the artificial intervertebral discs as described herein is surgically implanted between adjacent spinal vertebrae in place of a damaged disc. Those skilled in the art will understand that the surgical technique for implanting the artificial discs involves partial or total removal of the damaged disc and distraction of the adjacent vertebrae by forcibly separating the vertebrae from one another to provide the necessary space for insertion of the disc. The plates 10, 12 are slipped into place between the vertebrae with their fins 16 entering slots cut in the opposing vertebral surfaces to receive them. The plates may be inserted simultaneously with or without the core. After partial insertion of the disc, the individual plates 10, 12 can be further advanced independently or together to a final position. Once the disc has been inserted, the vertebra move together to hold the assembled disc in place.

The vertebral contacting surfaces of the plates 10, 12 including the teeth 20 and the serrations 18 locate against the opposing vertebrae and, with passage of time, firm connection between the plates and the vertebrae will be achieved as bone tissue grows over the serrated finish. Bone tissue growth will also take place about the fins 16 and through the holes 22 therein, further enhancing the connection which is achieved.

While the exemplary embodiments have been described in some detail, by way of example and for clarity of understanding, those of skill in the art will recognize that a variety of modifications, adaptations, and changes may be employed. Hence, the scope of the present invention should be limited solely by the appended claims.

What is claimed is:

1. An intervertebral disc comprising:
   an upper plate having an upper vertebra contacting surface and a lower bearing surface, wherein the upper vertebra contacting surface of the upper plate comprises a vertebral contacting surface formed in a first plane, a convex central portion extending upward from the first plane and at least one anchoring element extending upward beyond an upper surface of the convex central portion, and wherein the lower bearing surface has a concavity disposed opposite the convex central portion;
   a lower plate having a lower vertebra contacting surface and an upper surface; and wherein the lower vertebra contacting surface of the lower plate comprises a vertebral contacting surface formed in a second plane and a convex central portion extending downward from the second plane, and wherein the upper bearing surface has a concavity disposed opposite the convex central portion;
   a core positioned between the upper and lower plates, the core having upper and lower convex surfaces configured to mate with the bearing surfaces of the upper and lower plates; and
   a plurality of teeth provided on the upper surface of the upper plate and the lower surface of the lower plate, wherein the teeth having a posterior facing surface formed at an angle of less than 40 degrees with respect to the vertebra contacting surfaces and an anterior facing surface formed at an angle of more than 50 degrees with respect to the vertebra contacting surfaces.

2. The disc of claim 1, wherein the core is movable with respect to the upper and lower plates.

3. The disc of claim 1, wherein the at least one anchoring element is a first fin having a height greater than a width.

4. The disc of claim 3, wherein the first fin has a length greater than the height.

5. The disc of claim 3, further comprising a second fin on the lower plate extending from the lower surface of the convex central portion.

6. The disc of claim 1, wherein the plurality of teeth are not positioned on the convex central portions of the upper and lower plates.

7. The disc of claim 6, wherein the teeth are positioned in a symmetrical pattern adjacent to the convex central portions of the upper and lower plates.

8. The disc of claim 1, wherein the convex central portions are dome shaped portions.

9. The disc of claim 8, wherein the dome shaped portions have a diameter of about 5 to about 20 mm.

10. The disc of claim 1, comprising a plurality of finlets provided on the upper surface of the upper plate and the lower surface of the lower plate.

11. An intervertebral disc comprising:
    an upper plate having an upper vertebra contacting surface and a lower surface, wherein the upper surface of the upper plate has at least one anchoring fin extending from the upper surface of the upper plate;
    a lower plate having a lower vertebra contacting surface and an upper surface; and, wherein the lower surface of the lower plate has at least one anchoring fin extending from the lower surface of the lower plate;
    a plurality of teeth positioned in a symmetrical pattern on opposite sides of the anchoring fins of the upper and lower plates, the plurality of teeth each having a first surface and a second surface opposite the first side surface, wherein the first surface is formed at an angle of less than 40 degrees with respect to the vertebra contacting surfaces and the second surface is formed at an angle of more than 50 degrees with respect to the vertebra contacting surfaces;
    a plurality of serrations surrounding the plurality of teeth, wherein the plurality of serrations have a height at least 25 percent lower than a height of the teeth; and
    wherein the upper plate articulates with respect to the lower plate.

12. The disc of claim 11, wherein the anchoring fins have a length greater than their heights.

13. The disc of claim 11, further comprising a core positioned between the upper and lower plates, wherein the core is movable with respect to the upper and lower plates.

14. The disc of claim 11, wherein the at least one fin on one of the upper and lower plates comprises two parallel fins.

* * * * *